US00PP33515P2

(12) United States Plant Patent
Whitcomb

(10) Patent No.: US PP33,515 P2
(45) Date of Patent: Sep. 28, 2021

(54) ***HEPTACODIUM MICONIOIDES* PLANT NAMED 'WHIT LXXXI'**

(50) Latin Name: *Heptacodium miconioides*
Varietal Denomination: Whit LXXXI

(71) Applicant: Lacebark, Inc., Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 17/140,710

(22) Filed: Jan. 4, 2021

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./216, 226
See application file for complete search history.

(56) References Cited

U.S. PATENT DOCUMENTS

PP30,763 P3 * 7/2019 Wood ..... A01H 6/00
Plt./216

* cited by examiner

*Primary Examiner* — Susan McCormick Ewoldt
*Assistant Examiner* — Karen M Redden
(74) *Attorney, Agent, or Firm* — Jeffrey L. Streets

(57) ABSTRACT

A new and distinct *Heptacodium miconioides*, Fall Festival Tree aka Seven Sons Flower, designated cultivar 'Whit LXXXI' providing year round interest in the landscape. The color begins with early emergence of dark green leaves, followed by a floral show of flowers in late summer or early fall, large concentrations of fragrant white flowers, then after flowers fall, sepals elongate from barely visible to ⅜ to ⅝ inch and turn crimson creating a second flower-like show in the landscape then after the sepal show is stopped and leaves drop due to frost, the outer bark sloughs off revealing white bark that remains a color show in the landscape until early spring when leaves emerge again. 'Whit LXXXI' is cold hardy to −30 F., but also does well where little or no frost occurs, roughly zones 4 through 9. Free of disease or insect problems.

5 Drawing Sheets

Genus, species: *Heptacodium miconioides*.
Varietal denomination: 'Whit LXXXI'.

BACKGROUND OF THE INVENTION

Field of the Invention

The present invention relates to a new and distinct variety or cultivar of the ornamental small tree, *Heptacodium miconioides*, commonly known as Fall Festival Tree or Seven Sons Flower.

Description of the Related Art

*Heptacodium miconioides* is native to China. It was first discovered and reported to the West by E. H. Wilson in 1907 while working as a plant collector for the Arnold Arboretum. Information about the plant is limited. For example, the Flora of China, Volume 19, Translated by the Missouri Botanical Garden Press, 2011, contains only a few generalities, followed by a footnote: This is a rare species.

*Heptacodium miconioides* is very cold hardy. A specimen of unknown origin in Fort Atkinson, Wis. endured −30 degrees F. (Fahrenheit) in 2018 with no injury and excellent performance in 2019. A plant collection expedition to China in 1980 reported finding a plant growing in a very mild region, approximately equivalent to USDA hardiness zone 10 [Arnoldia vol. 46 (4) 2-14, 1986].

The information set forth in this plant patent application is based on research conducted in north central Oklahoma over a period beginning in 2004. Broad general features of *Heptacodium miconioides* seedlings are unique from most other plants. For example, *Heptacodium miconioides* seedlings are first to produce leaves in the spring and begin flower bud development in May, but flowers do not open until late August or early September. Then, after the white flowers drop, the collection of sepals surrounding a receptacle that contained from 3 to 9 flowers, dramatically increase in size and turn various shades of red, red-purple or pink creating a second show in the landscape. The bark typically remains various shades of tan to light brown, then sloughs off when growth begins in spring.

The following description is of the new and distinct Fall Festival Tree seedling, also called Seven Sons Flower, *Heptacodium miconioides* plant which has been given the cultivar name 'Whit LXXXI'. Specific color designations set forth by number designations are in accordance with The Royal Horticultural Society Colour Chart (1966). General color recitations are consistent with ordinary American color terminology.

The following botanical characteristics and observations are taken from 'Whit LXXXI' cultivar grown under normal outdoor conditions in north central Oklahoma. Unless, otherwise noted, the following description is of 'Whit LXXXI' plants propagated asexually from the original parent plant grown in a field near Stillwater, Okla.

SUMMARY OF THE INVENTION

The new and distinct variety of *Heptacodium miconioides* given the cultivar name 'Whit LXXXI' was selected from about 4,000 seedlings in a planned breeding program begun in 2004. 'Whit LXXXI' grows as a compact small tree with a height of 16 feet and spread of 21 feet at age 11 years if allowed to grow unpruned. 'Whit LXXXI' has leaves that emerge early, before most other genera of plants, retains showy dark green foliage throughout the growing season, flower buds are visible in early May, but flowers do not open until late August or early September. White and very fragrant flowers are in large loose panicles over the outer perimeter of the tree and last for 10 to 16 days depending on weather conditions, but after flowers fall, the sepals which are barely visible at the time of flowering, begin to expand reaching a length of ⅜ to ⅝ inch and turn crimson and remain that color until a freeze in late fall. After a freeze and leaves drop, stems ½ to ¾ inch or larger in diameter begin to slough off the outer bark exposing inner bark that is at first an off-white color, but with exposure to full sun, turns distinctly white and remains white until growth begins the following spring.

PARENT COMPARISON

Plants of the new cultivar 'WHIT LXXXI' are similar to plants of the original three purchases plants of unknown origin and other *Heptacodium* seedling in most horticultural characteristics, however, plants of the new cultivar 'WHIT LXXXI' differ by exhibiting the following unique characteristics:

1. Early to develop flowers and subsequent sepal show compared to the three original purchased plants and all of *Heptacodium* seedlings grown since 2004. For example, FIG. 1 shows 'WHIT LXXXI' cultivar with full sepal show with seedlings on either side providing little sepal color.
2. White bark in winter is a highly desirable landscape characteristic as it provides distinct contrast to broadleaf and coniferous evergreens. In searching the literature on this unique species, no mention of white bark could be found.
3. Grows as a small tree slightly wider at the base than tall if lower limbs are not removed.
4. Few or no suckers are produced by the asexually propagated offspring. Adventitious sucker growth is a major problem with a large percentage of seedlings grown during this research.

COMMERCIAL CULTIVAR COMPARISON

Plants of the new cultivar 'Whit LXXXI' are similar to the commercially available *Heptacodium miconioides* plant cultivar 'SMNHMRF', which is the subject of U.S. Plant Pat. No. 30,763 and sold under the trademark Temple of Bloom®, in most horticultural characteristics, however, plants of the new cultivar 'Whit LXXXI' differ in exhibiting the following unique characteristics:

1. The bark of the new cultivar 'Whit LXXXI' is distinctly white, 155 A or B, in winter versus U.S. Plant Pat. No. 30,763 described as greyed-orange, 166 B.
2. 'Whit LXXXI' grows as a small tree slightly broader than tall, about 16 feet tall by 21 foot spread at age 11 years when allowed to grow unpruned versus U.S. Plant Pat. No. 30,763 described as a perennial shrub or small tree, with only data provided from plant growing in containers.
3. Flowering and sepal show of 'Whit LXXXI' is earlier than the other 4,000 seedlings grown in a field in Oklahoma. No side by side growth and flowering comparison has been made with U.S. Plant Pat. No. 30,763 under similar conditions in Oklahoma.
4. Sepals of 'Whit LXXXI' are crimson ranging from red group 52 A to red-purple group 57 A versus U.S. Plant Pat. No. 30,763 described as red-purple 60-C.

DETAILED BOTANICAL DESCRIPTION

The plant:

*Type*.—Deciduous woody small tree.

*Classification*.—*Heptacodium miconioides*, Fall Festival Tree, or Seven Sons Flower.

*Growth habit*.—'Whit LXXXI' grows with multiple upright stems with low branches creating a broad rounded form typically slightly wider than tall if allowed to grow unpruned.

*Origin*.—The parent was an open pollinated seedling grown from a mixture of seeds collected from three original unnamed *Heptacodium* plants purchased from J. C. Raulston with North Carolina State University in 2004. As a result of mixing the seeds, the specific parent cannot be identified.

*Propagation*.—The new cultivar 'Whit LXXXI' has been propagated by softwood cuttings taken in spring and placed under intermittent mist in a greenhouse near Stillwater, Okla. Distinguishing characteristics of the asexually propagated offspring remain identical to the parent through succeeding asexual propagations.

*Size and shape*.—At age 8 years, 'Whit LXXXI' was about 12 feet tall with a spread of about 14 feet and at age 11 years, the tree is 16 feet tall with a spread of about 21 feet, when allowed to grow unpruned and comprised of multiple branches and with no undesirable sucker growth.

*Hardiness*.—The new variety of *Heptacodium miconioides* has not been tested over a wide range, but a large specimen of unknown origin in a landscape in southern Wisconsin endured −30 F. winter of 2018-2019 with normal growth the following spring. In addition, a specimen of 'Whit LXXXI' about 5 feet tall when planted in southern Wisconsin in 2018 has survived the winters of 2018/19 and 2019/20 with no winter damage and normal growth each spring. A specimen of 'Whit LXXXI' planted near Brownsville, Tex. has also performed well. It is unlikely that the new cultivar 'Whit LXXXI' will vary in cold tolerance compared to other unnamed *Heptacodium miconioides* plants growing in a variety of locations across the USA.

*Pests, diseases and adaptation*.—Foliage among all 4,000 seedlings and including the new cultivar 'Whit LXXXI' has remained free of damage from insect pests, even grasshoppers and no diseases have been observed since this research began in 2004. Deer occasionally strip leaves from a branch, but damage is local and minor. 'Whit LXXXI' has been planted over a range of soils ranging from deep sand to clay loam and has performed well. Growth and flowering have been best in full sun. Growth and foliage development remains good in partial shade, but flowering is reduced.

Figure 1:
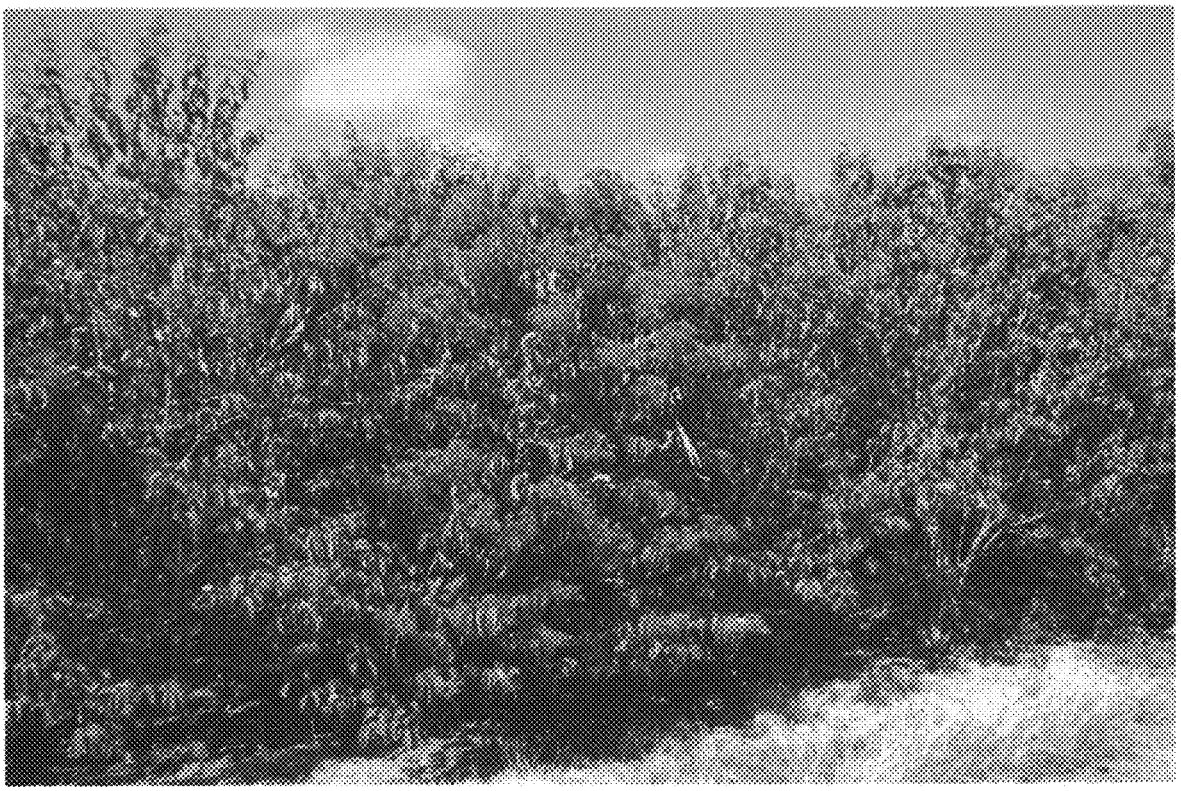
FIG. 1 is a full color photographic view of the new *Heptacodium miconioides* plant named 'Whit LXXXI' at age 8 years in full early Fall sepal show compared to adjacent plants and with rounded crown form and dense foliage extending to the ground.
Figure 2:
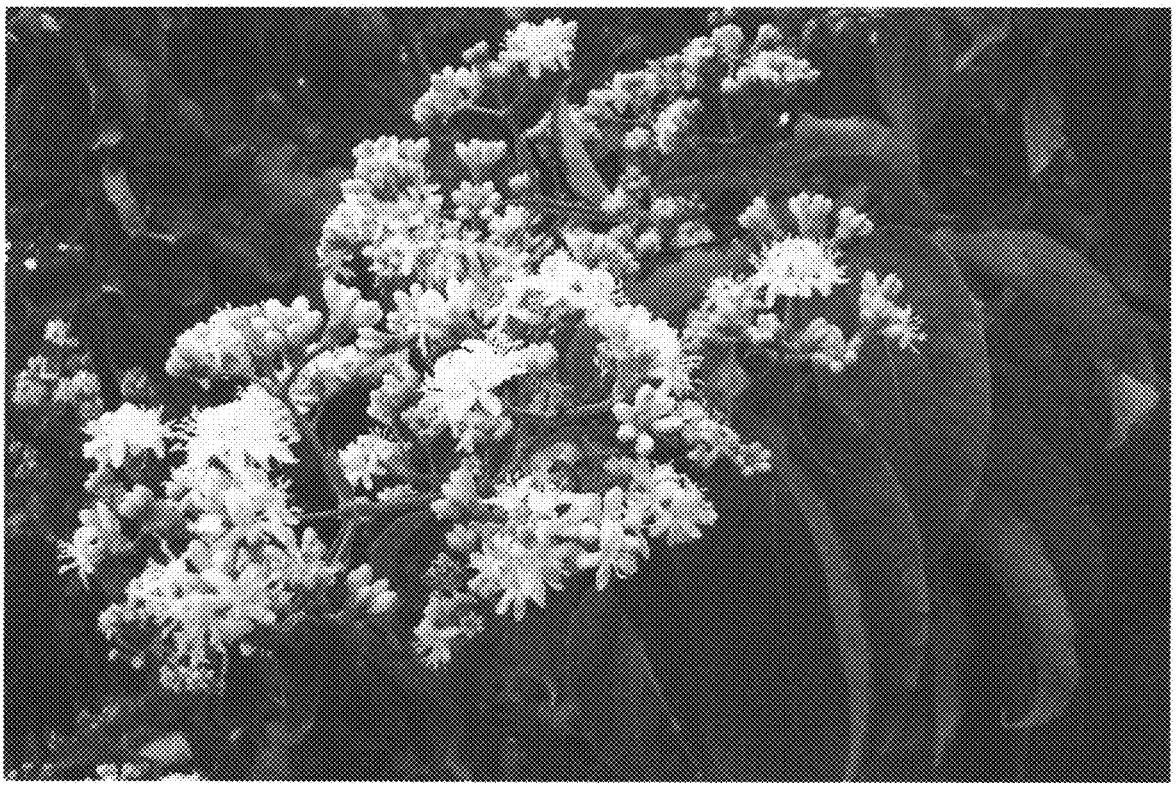
FIG. 2 is a full color photographic view of the new *Heptacodium miconioides* plant named 'Whit LXXXI' showing a complex panicle of white flowers at tips of branches and background of dense foliage.
Figure 3:
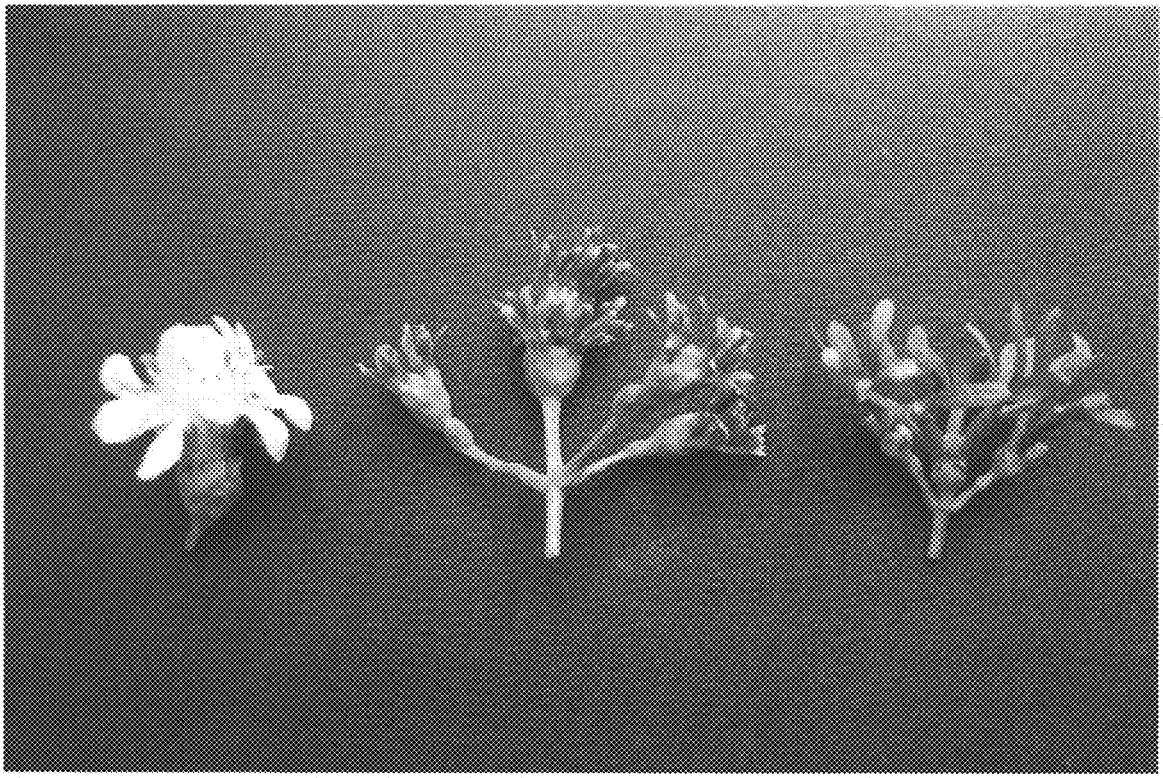
FIG. 3 is a full color photographic view of the new *Heptacodium miconioides* plant named 'Whit LXXXI' showing several white flowers in a complex receptacle (left), several receptacles from ends of branches seven days after flowers drop showing early extension of sepals (center) and full extension of sepals after 14 days (right). This photo comparison showing flowers to sepal full development was made using flowers and early sepal development from heavily shaded branches.

Flowering and sepal development:

*Blooming period*.—The blooming period/floral show for 'Whit LXXXI' is early relative to other *Heptacodium miconioides* seedlings grown during this research (FIG. 1) and overall floral show is most unusual and extends over about 60 days including 10 to 16 days of white, fragrant, flowers (FIG. 2), with an interruption of 12 to 16 days until full coloration of the calyx (FIGS. 1 and 3) which can then last 30 to 40 days or longer. Flower bud development at tips of twigs begins in early May, and slowly expands during the growing season to form large, variable size, complex panicles about 10 to 14 inches wide by 12 to 18 inches long, creating a massive show of fragrant, white flowers, white-group 155 A or B, opening first at the base of the panicle and progressing upwards. Flowers do not open until late August or early September near Stillwater, Okla. varying moderately with weather conditions, and remain showy about 10 to 14 days. After flowers drop, the receptacles about 5/32 to 9/32 inch in diameter remain with only a small portion of the sepals visible (FIG. 3), then during a period of about 10 to 14 days, sepals, (collectively, corollas), form calyces, a specialized petal that wraps around the fruit, expand to about 3/8 to 5/8 inch and turn crimson and remain showy until a hard freeze in late October or early November. Fruits at the base of the sepal are about 5/32 to 9/32 inch long and about 3/32 diameter, with many containing only empty seed coats. Individual flowers typically have five petals, occasionally four, arranged in a whorl, with each petal elongated, about 1/4 inch long and about 1/8 inch wide, with parallel margins, rounded tip and truncated base and smooth surfaces and margins and white in color about 155 B or C on both upper and lower surfaces. Anthers are about green-group 153 A; filaments are clear, opaque matching no color reference; and stigma is just a clear dot among the petals. Flowers are arranged three to nine, in complex receptacles with five or six being most common. When flowers fall, sepals are very small and inconspicuous, then sepal expansion begins (best shown in FIG. 3) and continues until the sepals create a structure resembling the original flowers. Another unique aspect of the sepal show of 'Whit LXXXI' is when sunlight is directly on the sepals and viewed from the front the color is dark crimson, red group, 52 A, ranging to red- purple group 57 A (FIG. 1) on both upper and lower surfaces. However, when viewed from the back or looking up into a panicle, or on an overcast day the color is typically red group 52 B, C or D (see FIG. 3). Sepals are arranged in whorls like the flowers, only fused at the base, with individual sepal size variable, but about 3/8 to 5/8 inch long, and about 3/8 inches wide, with rounded tip, fused to the complex at the base, and smooth margins approximately parallel. At time of approaching Fall freeze, seeds are immature with seeds ranging from near white, 158 A to yellowish, 160 A or B, and about 1/4 to 3/8 inch long and about 1/8 to 3/16 inch in diameter and are contained in the base of the sepal complex. When a freeze occurs, the seeds abruptly shrivel and turn brown, about 177 A or B.

Figure 4:
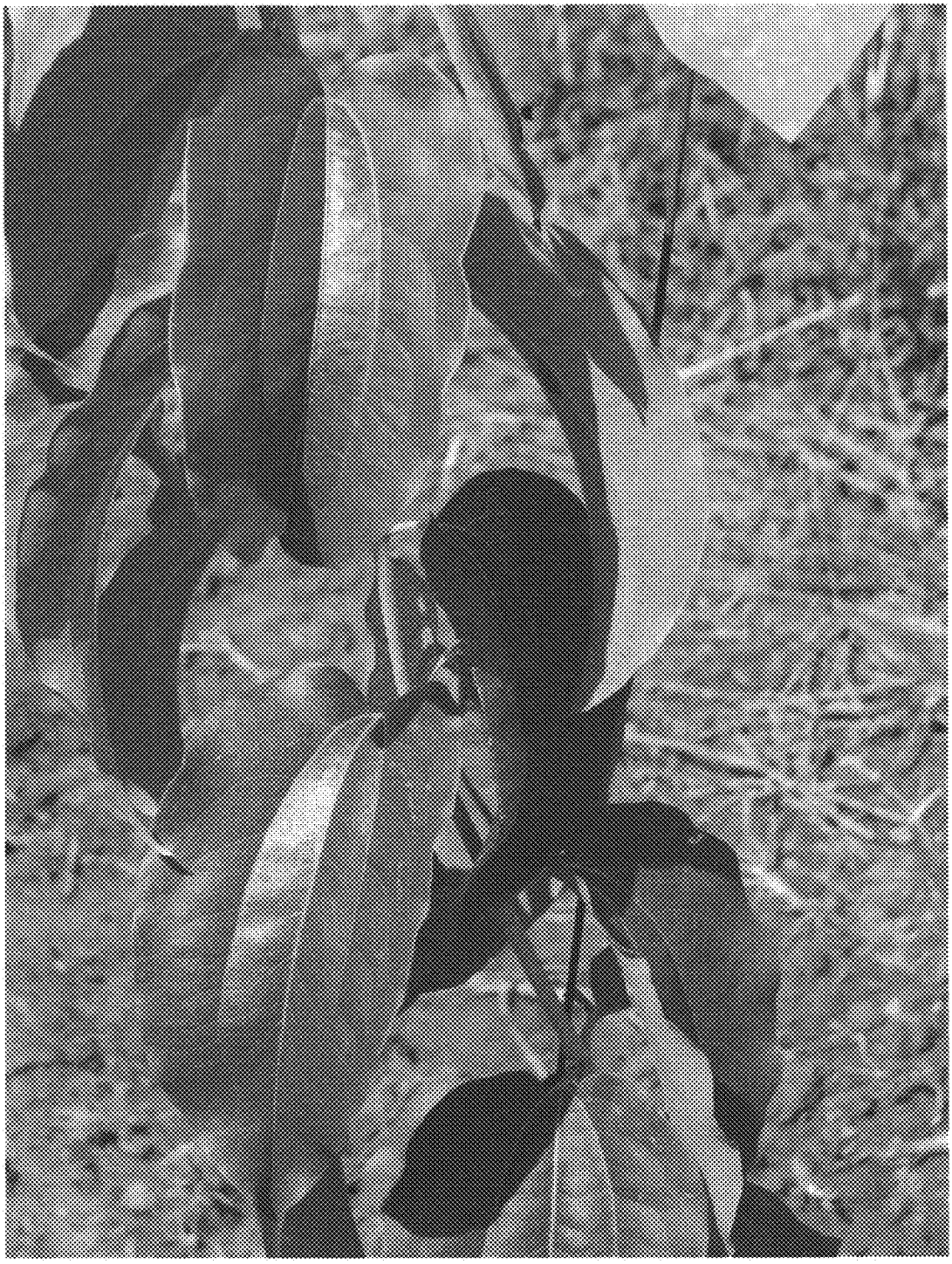
FIG. 4 is a full color photographic view of the new *Heptacodium miconioides* plant named 'Whit LXXXI' showing smooth, glossy leaves in full sun. Leaves remain dark green and attractive and free of insect damage or disease the entire growing season.

*Foliage*.—Leaves on new growth emerge early in the growing season, tolerate a wide array of conditions, including late spring freezes, heat, dehydrating winds and full sun remaining attractive until late fall, dropping irregularly with no color change. Leaves are simple, opposite, two ranked, large, about 2.5 to 3.5 inches wide by 3.5 to 7.0 inches long, ovate, acuminate at the tip and truncated at the base, with distinct trinerved veins parallel to the smooth margin and supported by short, stout petioles about 1/2 to 3/4 inch long (FIG. 4). Leaf color including petiole, on both upper and lower surfaces ranges from yellow-green group 144 A, B or C early in the season or when in partial shade, transitioning to 147 A, B or C. Leaves are retained late into the fall before dropping with no fall color. Leaf texture is smooth, glabrous on both upper and lower surfaces.

Figure 5:
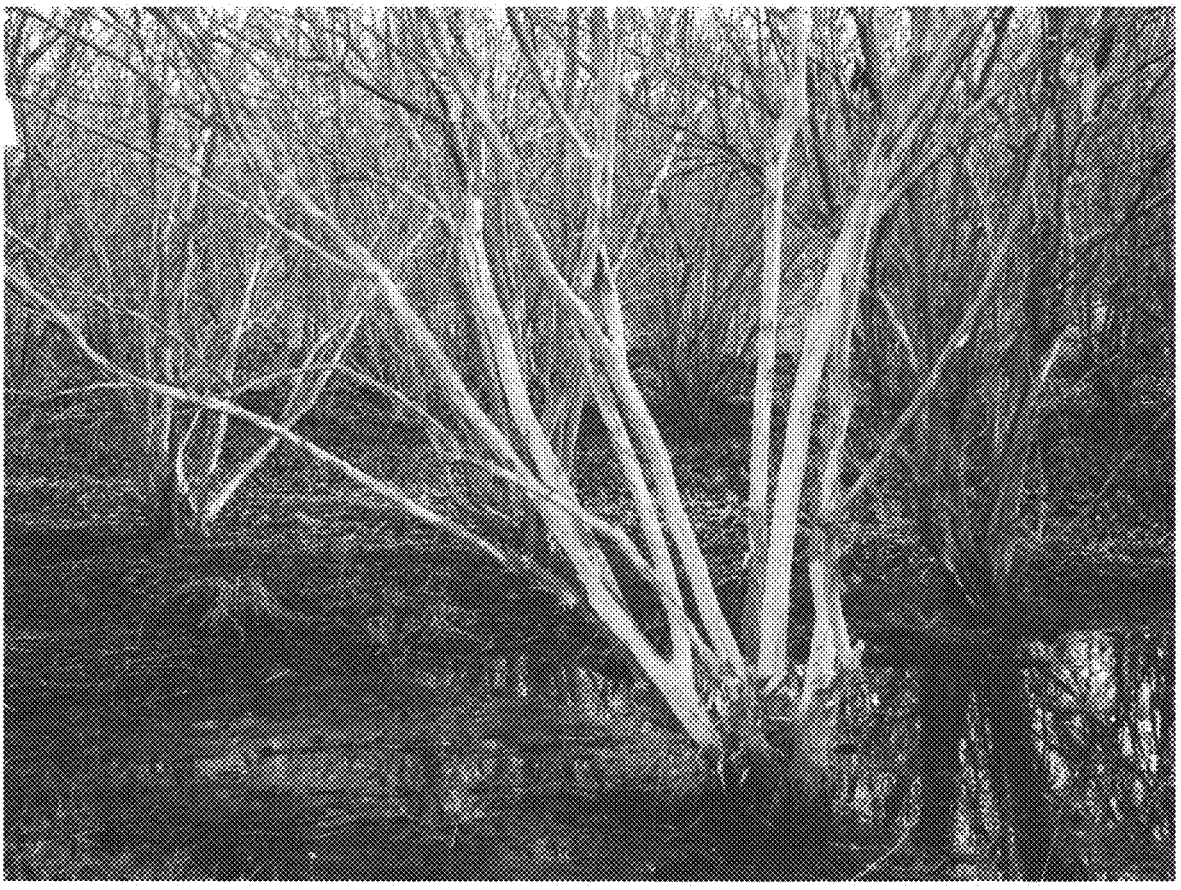
FIG. 5 is a full color photographic view of the new *Heptacodium miconioides* plant named 'Whit LXXXI' at an age of 8 years, showing distinct white bark in winter after leaves have fallen and contrasting with other seedlings the same age with brown bark in the background.

*Twigs, bark and suckers*.—Current seasons normal twig growth as well as sucker growth (see below) begins about yellow-green group 144 A, B or C, varying with sun exposure, darkening to about yellow-green group 146 A or B or 147 A or B, transitioning during the growing season to about greyed-orange group 165 A or B as stems increase in diameter up to about 1/2 to 3/4 inch. The second growing season, normal growth twigs continue, about greyed-orange group 165 A or B, until late in the growing season, when bark exfoliation begins like older stems. Bark development on older stems, those 1/2 to 3/4 inch diameter and larger is transitional during the year: Winter bark is white, about 155 A or B until early spring, (FIG. 5) when bark color begins to change to about greyed-white group 156 A or B, then gradually to about greyed-green group 195 D or C, then as the season continues, bark color transitions to about greyed-green group 197 D or C, progressing to about grey-brown group 199 D and finally to about greyed-orange group 164 A or B or 165 A or B, and remains until mid fall when bark begins to slough off in strips as a result of rapid stem diameter increase, exposing the inner bark about greyed-white group 156 B or C then with dropping of leaves and more exposure to sun, resulting in winter white bark about 155 A or B. The new cultivar, 'Whit LXXXI' develops few or no suckers (FIG. 5), unless the terminal shoot is damaged such as grazing by deer, but removal of those suckers by pruning does not stimulate additional sucker growth. Any suckers that develop have coloration the same as described for twigs. For comparison, and as an example of why 'Whit LXXXI' is superior to other seedlings grown as part of this extensive research, suckers arise on all but an occasional *Heptacodium miconioides* seedling and may grow from a few feet to 12 feet or more in a single season and typically with no side branches. Suckers are vigorous adventitious shoots that arise from activation of dormant buds on twigs and stems of all ages. As of 2020, and having grown over 4,000 seedlings from various parents, it is the rare exceptional seedling tree that remains free of suckers such as 'Whit LXXXI'. White bark coloration in winter is exceptional for 'Whit LXXXI' (FIG. 5) relative to the other 4,000 seedlings grown as part of this research and unique compared to what is described in the literature. For example, The Flora of China, Vol. 19 notes young branches are red-brown. U.S. Plant Pat. No. 30,763 by Wood describes bark as brown, grayed-orange group 166 B. Chicago Botanic Garden plant profile, describes bark as light brown that exfoliates to expose a deeper brown beneath. Gary Koller, writing in Arnoldia, Journal of the Arnold Arboretum, vol. 46, 1986, notes stems produce thin bark that peels in small paper like strips and, in winter, plants have light tan to brown bark.

I claim:

1. A new and distinct variety of *Heptacodium miconioides* plant named 'WHIT LXXXI' substantially as illustrated and described herein.

* * * * *